United States Patent
Eisen et al.

(10) Patent No.: US 6,297,044 B1
(45) Date of Patent: Oct. 2, 2001

(54) MINIMALLY INVASIVE APPARATUS FOR TESTING LESIONS OF THE ORAL CAVITY AND SIMILAR EPITHELIUM

(75) Inventors: Drore Eisen, Cincinnati, OH (US); Stephen Frist; Joel Recht, both of Monsey, NY (US)

(73) Assignee: Oralscan Laboratories, Inc., Suffern, NY (US)

(*) Notice: Subject to any disclaimer, the term of this patent is extended or adjusted under 35 U.S.C. 154(b) by 0 days.

(21) Appl. No.: 09/298,219

(22) Filed: Apr. 23, 1999

Related U.S. Application Data

(60) Provisional application No. 60/121,255, filed on Feb. 23, 1999.

(51) Int. Cl.[7] .............................. C12M 1/26; C12M 1/34
(52) U.S. Cl. ..................... 435/287.1; 435/288.7; 435/309.1; 382/133; 600/569
(58) Field of Search ................. 435/29, 40.5, 40.51, 435/287.1, 287.3, 287.9, 288.7, 309.1; 600/569–572; 382/133

(56) References Cited

U.S. PATENT DOCUMENTS

| | | | |
|---|---|---|---|
| 2,839,049 | * | 6/1958 | Maclean . |
| 2,955,591 | * | 10/1960 | Maclean . |
| 4,965,725 | * | 10/1990 | Rutenberg . |
| 5,184,626 | * | 2/1993 | Hicken . |
| 5,257,182 | * | 10/1993 | Luck et al. . |
| 5,287,272 | * | 2/1994 | Rutenberg et al. . |
| 5,333,207 | * | 7/1994 | Rutenberg . |
| 5,544,650 | * | 8/1996 | Boon et al. . |
| 5,625,705 | * | 4/1997 | Recht . |
| 5,629,766 | * | 5/1997 | Kaplan . |
| 5,655,029 | * | 8/1997 | Rutenberg et al. . |
| 5,659,421 | * | 8/1997 | Rahmel et al. . |
| 5,740,270 | * | 4/1998 | Rutenberg et al. . |
| 5,978,497 | * | 11/1999 | Lee et al. . |

* cited by examiner

Primary Examiner—William H. Beisner
(74) Attorney, Agent, or Firm—Levisohn, Lerner, Berger & Langsam

(57) ABSTRACT

A non-lacerational method and system employing an abrasive brush for obtaining a transepithelial sample of an epithelial lesion which may be keratinized is disclosed in which an analytical system including an imaging system is provided to detect precancerous and cancerous cells. The transepithelial non-lacerational brush produces sufficient cells from all three layers of the epithelium so that an analytical system comprising a programmed computer can detect which cells require further examination because of a likely suspicion of said pre-cancerous and cancerous conditions. The method and system can apply to the diagnosis non-cancerous conditions as well.

60 Claims, 7 Drawing Sheets

US 6,297,044 B1

MINIMALLY INVASIVE APPARATUS FOR TESTING LESIONS OF THE ORAL CAVITY AND SIMILAR EPITHELIUM

This application claims benefit of Provisional Patent Application No. 60/121,255 filed Feb. 23, 1999.

FIELD OF THE INVENTION

The present invention is directed to a minimally invasive apparatus and method for testing lesions of the oral cavity and similar epithelium.

BACKGROUND OF THE INVENTION

Between 5% to 10% of patients in general dental and medical practice have harmless appearing oral lesions which are routinely noticed on oral examination, or which are incidentally observed while performing a cosmetic or other dental procedure. Visual inspection and palpation of these lesions to detect early stage oral cancer is highly unreliable. This is because benign, dysplastic and cancerous lesions are often indistinguishable from each other on clinical inspection. The vast majority of these relatively benign appearing lesions are, in fact, benign. However, at least 6% of these benign appearing lesions may be pre-cancerous or cancerous, and failure to identify these dangerous lesions at an early, treatable stage, is a primary factor in the currently low five-year survival rate for oral cancer.

The dentist or physician who visually detects an oral lesion which is not clearly suggestive of precancer or cancer is faced with a quandary when restricted to the methods and apparatus of the prior art. The only accurate tool currently believed to be available in the prior art to distinguish benign from pre-cancerous and cancerous oral lesions is a lacerational or scalpel biopsy of the lesion followed by histological examination of the excised tissue. In a scalpel biopsy, a variety of surgical cutting instruments are used to obtain a tissue sample. If such a scalpel biopsy removes a part of the lesion it is referred to as an "incisional" biopsy, while if it removes the entire lesion it is referred to as an "excisional" biopsy.

In either case, a scalpel biopsy is a painful, lacerational, highly invasive procedure. Typical instruments for this purpose include, but are not limited to a flat scalpel blade, a round scalpel blade (punch biopsy) and scissors. Local anesthesia is always required. Considerable bleeding from the wound is common and suturing is often necessary. For these reasons, primary care dentists and physicians, those clinicians who most often encounter benign appearing oral lesions, are reluctant to perform a scalpel biopsy. When necessary, these clinicians will therefore generally refer the patient to an oral surgeon or oral pathologist for the procedure. Since as many as 5% to 10% of all patients in a typical dental or general adult medical practice may have such visible oral lesions, many of which are likely to be benign, performing a scalpel oral biopsy in the primary care setting or referral to a specialist for such performance is reserved for only the most clinically suggestive lesions. Yet, as has repeatedly been shown, pre-cancerous and cancerous oral lesions often mimic benign lesions. Lacking the subject invention, these precancerous or cancerous, but benign appearing, oral lesions typically do not receive any immediate diagnostic evaluation and are thus allowed to progress to an advanced stage of oral cancer. Once such progression is underway and continues untreated, the patient's chances for recovery diminishes.

A prior art approach which has attempted to address this problem in testing lesions of the oral cavity was the use of cytology. In this approach, a sample of cells which was naturally exfoliated from the surface of a lesion into mucous or saliva is examined microscopically. While cytology is commonly used to detect precancer and cancer in other body sites, it has not proven to be useful in the oral cavity because of its low sensitivity, i.e. its high false negative rate. It is believed that this high false negative rate is in part due to the fact that many oral lesions have an overlying keratin layer which limits availability to the lesion surface of naturally exfoliated abnormal cells. In one large study, oral cytology was found to have a false negative rate of 30%. This means that 30% of oral lesions determined to, in fact, be precancerous or cancerous on scalpel biopsy and histology were falsely reported as "negative" using oral cytology. Due to its unreliable sensitivity, prior art cytologic technique is rarely used to test oral lesions or similar keratinized epithelial lesions for precancer or cancer.

SUMMARY OF THE INVENTION

In accordance with the invention, a cytological or cellular sample of an oral lesion is taken from a patient for analysis. In one embodiment, this sample is obtained by means of a non-scalpel instrument which is sufficiently abrasive to penetrate all three layers (basal, intermediate, and superficial) of the oral epithelium. In the preferred embodiment, this trans-epithelial sample is obtained by means of pressing and rotating a circular stiff nylon brush several times over the entire lesion surface. Alternatively, the sample can be obtained using cytology or histology, and can be any cellular specimen, including cells sloughed off naturally, or cells removed by a health care professional, including a tissue specimen or oral biopsy.

As an alternative or additional feature of the subject invention, a cellular sample (preferably trans-epithelial) is examined with the aid of an image recognition system designed to identify minimal evidence of pre-cancerous and cancerous change. In accordance with the invention, the system can detect small numbers of abnormal cells distributed among the large number of normal cells obtained during the sampling procedure.

In this alternate or additional embodiment, the subject invention preferably overcomes the limitations and difficulties associated with analysis of cellular specimens for abnormal characteristics by providing an image recognition system which detects characteristics relating to abnormal keratinization of the cells. Preferably, these characteristics include color saturation associated with such abnormal keratinization.

In the preferred embodiment, the subject invention overcomes the sensitivity limitations of prior art oral cytologic technique by combining both innovations in oral pathology, namely: 1) a non-scalpel cellular sample of all three layers of the oral epithelium; and 2) subjecting this novel sample to inspection by the novel image recognition system specifically designed to detect minimal evidence of early pre-cancerous change in a trans-epithelial sample from an oral lesion, or other lesion with similar epithelia. This novel image recognition system preferably analyzes for the presence of abnormal keratinization, by detecting predetermined characteristics of color saturation.

For purposes of this patent application, the prior art scalpel procedure is defined as lacerational, whereas the novel invention herein is non-lacerational and therefore minimally invasive. To the extent that an abrasive brush has characteristics that may cause minor discomfort and/or bleeding, there is substantial difference between the prior art scalpel trauma and the minimal trauma associated with the present invention.

Thus, in the preferred embodiment of the invention, the image processing system combines: 1) sensitivity to the presence of abnormal cellular morphology obtained from any or all of the three layers of the novel trans-epithelial cellular sample with 2) sensitivity to the presence of abnormally keratinized cells as are commonly found in any or all of the three layers of the epithelia, and also obtained by means of the novel trans-epithelial cellular sample of the subject invention. Thus, the keratin component, which presented an obstacle to prior art oral cytology, is both penetrated, to ensure that any underlying abnormal basal cell morphology is available for analysis, and productively utilized, as a means of increasing the method's overall sensitivity to evidence of precancerous and cancerous change.

In a preferred embodiment, the image recognition system selects the most suspect abnormal cells and cell clusters among the sample, and displays these cells and cell clusters on a video monitor for expert review.

In the preferred embodiment, the image recognition system also provides a color printout of those suspect cells and cell clusters selected by the expert reviewer as representative of the case.

In the preferred embodiment, the image recognition system selects abnormal cells based on morphological characteristics and on overall resemblance to abnormal cells on which it has been trained.

In the preferred embodiment of the invention, the image recognition system is directed to detection of abnormality of the oral cavity by including a function to detect abnormal keratin as is often found in dysplastic and cancerous oral tissue.

In the preferred embodiment of the invention, the image recognition system is directed to detection of abnormal keratin by being programmed to detect a threshold level of color saturation associated with "hyalinization" or the stained appearance of such abnormal keratin.

In a further preferred embodiment of the invention, the image recognition is directed to the combination of morphological cellular change associated with pre-cancer and cancer and the appearance of abnormal keratin as produced by pre-cancerous and cancerous cells of the oral cavity and similar epithelia.

In one embodiment of the invention, the image recognition system may be constructed through modification of image recognition systems currently manufactured and sold to detect abnormal cells spontaneously exfoliated from non-keratinized lesions such as cervical lesions.

ADVANTAGES OF THE INVENTION OVER THE PRIOR ART

The invention consists of a method and system which for the first time provides accurate evaluation of oral lesions without requiring the performance of a scalpel biopsy. A primary objective of the subject invention is to accurately distinguish pre-cancerous and cancerous oral lesions from benign oral lesions without the pain, bleeding, and tissue wound that typically result from the prior art technique of scalpel biopsy and histology. In a multi-center clinical trial with over 800 patients performed at 35 U.S. Academic Dental Centers, the sensitivity and specificity of the subject invention was compared to the prior art technique of scalpel biopsy and histology. In this double blind study, the subject invention was found to detect 100% of the pre-cancerous and cancerous lesions detected by the prior art technique. The subject invention thus had a 0% false negative rate in this study. As noted above, this contrasts with false negative rates as high as 30% commonly associated with prior art oral cytology. In addition, the subject invention had less than a 1% false positive rate in this study. In this study, the subject invention also detected pre-cancer or cancer in approximately 15 patients whose lesions did not visually appear suspicious enough to expert examiners to warrant a scalpel biopsy. These outcomes represent lives that were potentially saved by the subject invention.

An additional advantage of the subject invention over the prior art diagnostic technique is greater sensitivity to the detection of pre-cancer and cancer in large multi-focal oral lesions. This is because of the larger sampling area obtained by the brush biopsy technique of the subject invention when compared to the smaller area sampled by a traditional incisional scalpel biopsy.

An additional advantage of the subject invention is that patients which have chronic oral lesions can have these lesions followed over time by repeated testing using a minimally invasive procedure.

An additional advantage of the subject invention is that it allows accurate, minimally invasive testing of lesions from areas of the body outside of the oral cavity where a keratin layer that limits the accuracy of prior art cytological technique may be present, Several such areas are the larynx, pharynx, esophagus, and vulva.

An additional advantage of the subject invention is that it allows diagnosis of non-cancerous conditions, such as candidiasis, herpes, geographic tongue, lichenplanus, human papilloma virus, and others.

DETAILED DESCRIPTION OF THE INVENTION AND THE PREFERRED EMBODIMENTS

Figure 1:
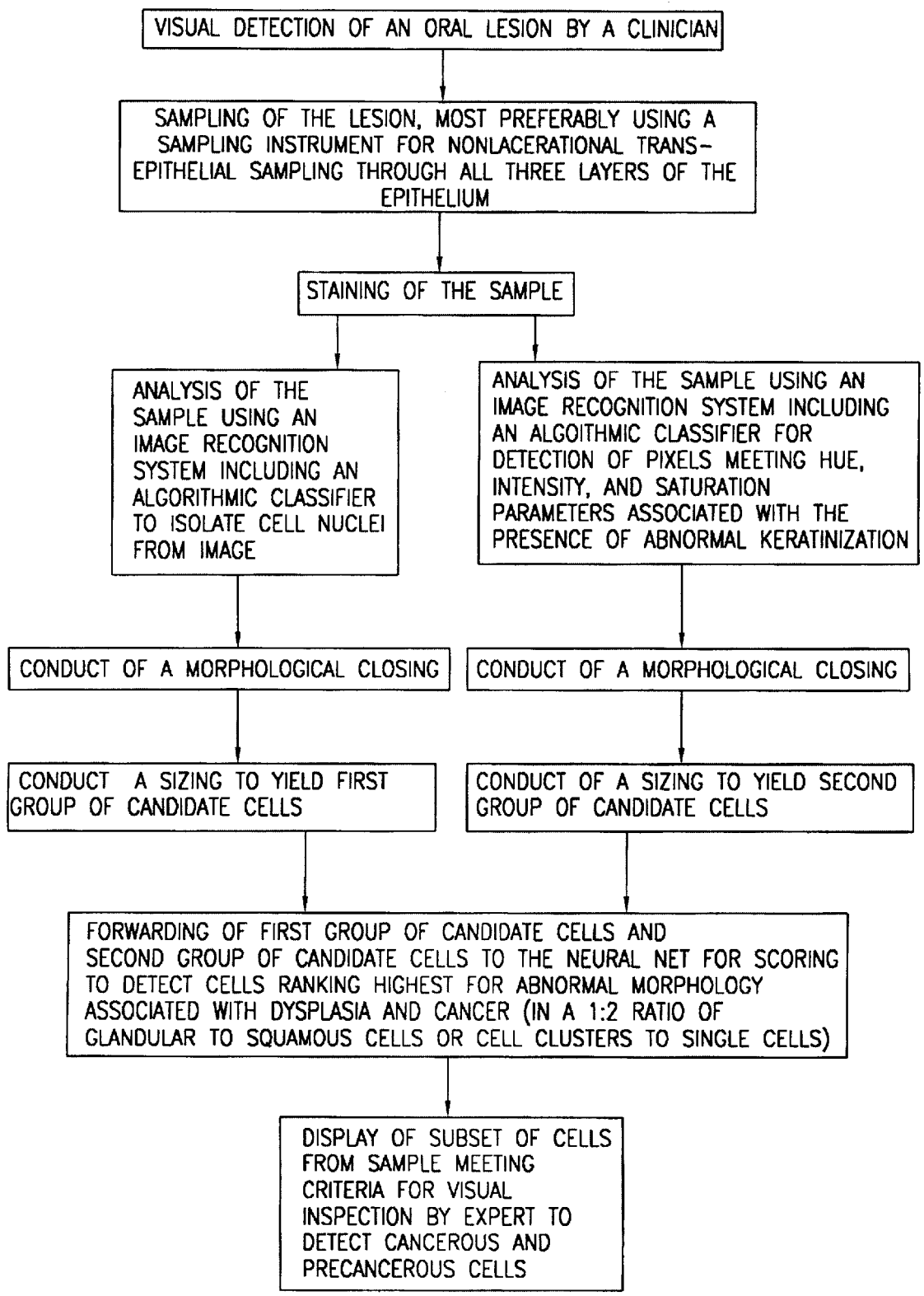
FIG. 1 is a flowchart illustrating the method of one embodiment of the present invention.

It is known that the functional differentiation of euplastic tissues to form keratinized stratified squamous epithelium is characterized by certain important morphological features. Frost, for example, discusses this differentiation, and the prototypical morphology at length. See, John K. Frost, The Cell in Health and Disease: An Evaluation of Cellular Morphologic Expression of Biologic Behavior, $2^{nd}$ edition, Chapter 11, in Monographs in Clinical Cytology, vol. 2 (New York: Karger 1986). Specifically, such cells display a central nucleus, a thread-like chromatin pattern, karyopyknosis with maturation, intercellular bridges, stratification, keratinization, thinning, orientation parallel to the basement membrane and lumen, and exfoliation as single cells.

In accordance with the present invention, an automated, computer implemented, system is provided for detection of such differentiation, particularly for cells of the oral cavity and similar epithelium. As such, the invention provides a means for alerting physicians to the presence of cancerous or precancerous cells at an early stage by overcoming the disadvantages of the prior art which has tended to avoid early detection.

Accordingly, in one embodiment of the present invention, a sample of cells from the oral cavity or similar epithelia is processed by an image analysis system for detection of characteristics associated with dysplasia or cancer. In a further embodiment of the invention, a standard sample of cells, taken as known in the prior art, is sent to an automated image processing system for detection of abnormal keratinization.

In accordance with the preferred embodiment of the invention, it is important that a transepithelial sample be taken from the oral cavity or similar epithelia, the sample being obtained using a nonlacerational sampling device. This cytological or cellular sample of the entire epithelial thickness of an oral lesion is obtained using a non-scalpel instrument which is sufficiently abrasive to penetrate all three layers (basal, intermediate, and superficial) of the oral epithelium, preferably the sampling instrument disclosed in U.S. Provisional Patent Application Ser. No. 60/093,910, filed Jul. 23, 1998 and entitled "Apparatus and Method for Performing a Non-Lacerating Biopsy of Lesions of the Oral Cavity and of Similar Epithelium", the disclosure of which is provided below, or the Spirabrush™, available from The Trylon Corporation of Torrance, Calif., or the like. In the preferred embodiment, this trans-epithelial sample is obtained by means of pressing and rotating a circular stiff nylon brush several times over the entire lesion surface. This sample is then analyzed by an automated image processing system for detection of morphology or characteristics typical of dysplasia or cancer.

In the preferred embodiment of the invention, the transepithelial sample is analyzed by an image processing system for detection of the presence of abnormal keratinization. In a further preferred embodiment, the sample is also analyzed for the presence of other characteristics or morphology associated with dysplasia or cancer.

Figure 4:
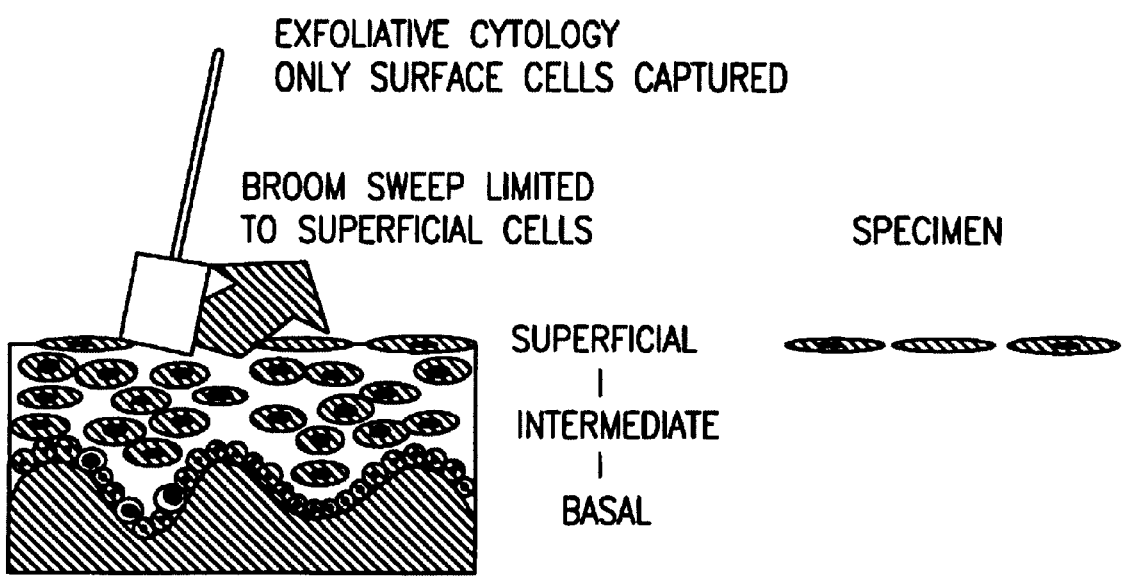
FIG. 4 is a cross sectional view of an section of epithelium including precancerous or cancerous cells, showing the extent of sampling obtained using exfoliative cytology.
Figure 5:
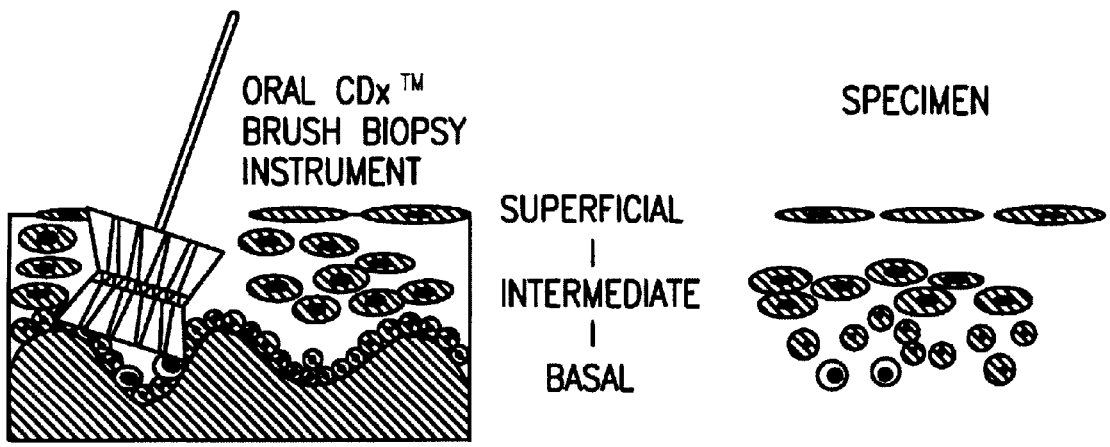
FIG. 5 is a cross sectional view of an section of epithelium including precancerous or cancerous cells, showing the extent of sampling obtained using the brush biopsy technique of the present invention.

As shown in FIG. 4, in the prior art method of exfoliative cytology, a non-abrasive sweep is conducted of the epithelial surface in a region of interest which typically only captures surface and exfoliated cells from the epithelial area. Abnormal cells 37 located below the surface, for example, cells located at the basal layer, will therefore often be missed using this superficial sampling. As a result, the specimen sent for analysis, will lack these deeper cells, and may therefore result in a false negative diagnosis. In accordance with the present invention, in contrast, a brush biopsy is taken, using the brush biopsy instrument disclosed, the brush being used to penetrate below the surface of the epithelium and obtain cells from all three epithelial layers. Thus, the specimen sent for testing includes abnormal cells regardless of whether they are cells from the superficial layer or the deeper intermediate and basal layers, providing a more complete and accurate cellular sample for analysis.

In the preferred embodiment, the subject invention thus combines two innovations in oral pathology, namely, a cellular sample of all three layers of the oral epithelium obtained without the use of a scalpel or similar lacerational instrument, with an analysis of that sample by a novel image recognition system specifically designed to detect minimal evidence of early precancerous change in that transepithelial sample from an oral lesion, or other lesion with similar epithelia. In the preferred embodiment of the invention, the image processing system combines sensitivity to the presence of abnormal cellular morphology obtained from any of the three layers of the epithelia with sensitivity to the presence of abnormally keratinized cells as are found in any of the layers of the epithelia. In contrast to the prior art, the keratin component, which previously presented an obstacle to prior art oral cytology, is penetrated to ensure that any underlying abnormal intermediate and basal cell morphology is available for analysis and productively utilized as a means of increasing the method's overall sensitivity to evidence of precancerous and cancerous change.

In one preferred embodiment, the invention utilizes a modified version of the commercially available PAPNET system, currently sold by Neuromedical Systems, Inc. of Upper Saddle River, New Jersey and Suffern, New York. Further details of such systems are described in U.S. Pat. No. 4,965,725, entitled "Neural Network Based Automated Cytological Specimen Classification System and Method"; U.S. Pat. No. 5,257,182, entitled "Morphological Classification System and Method"; U.S. Pat. No. 5,287,272, entitled "Automated Cytological Specimen Classification System and Method"; U.S. Pat. No. 5,232,207, entitled "Inspection Apparatus and Method with Inspection Auditing for Images Presented on a Display"; U.S. Pat. No. 5,544,650, entitled "Automated Specimen Classification System and Method"; U.S. Pat. No. 5,625,705, entitled "Intensity Texture Based Classification System and Method"; U.S. Pat. No. 5,629,766, entitled "Global MTF Measurement System"; U.S. Pat. No. 5,655,029, entitled "Device and Method for Facilitating Inspection of a Specimen"; U.S. Pat. No. 5,659,421, entitled "Slide Positioning and Holding Device"; and U.S. Pat. No. 5,740,270, entitled "Automated Cytological Specimen Classification System and Method", the disclosures of which are fully incorporated herein by reference. In alternative embodiments, the invention utilizes a modified computer image recognition system having similar or equivalent capability to detect and present abnormal cells within certain predetermined parameters.

Currently, oral lesions which are routinely noticed on oral examination, or are incidentally observed while performing a cosmetic or other dental procedure, are only rarely biopsied or tested to detect early stage cancer. In accordance with the present invention, however, the dentist or physician, or other expert who visually detects such lesions can routinely test them to detect abnormality with a minimum of discomfort to the patient.

In accordance with the invention, such testing is conducted to obtain a transepithelial sample of the lesion which can them be sent for staining and subsequent analysis by a computer implemented system. Accordingly, in the first step of the present invention, a transepithelial sample is taken from the patient's oral lesion.

In accordance with the preferred embodiment of the invention, the cytological or cellular sample is taken of the entire epithelial thickness of an oral lesion by means of a nonlacerational or nonscalpel instrument which is sufficiently abrasive to penetrate all three layers (basal, intermediate, and superficial) of the oral epithelium.

Preferably, this trans-epithelial sample is obtained by means of pressing and rotating a circular stiff nylon brush several times over the entire lesion surface. In a preferred embodiment of the invention, the sample is taken using the brush disclosed in pending U.S. Provisional Patent Application Ser. No. 60/093,910, filed Jul. 23, 1998 and entitled "Apparatus and Method for Performing a Non-Lacerating Biopsy of Lesions of the Oral Cavity and of Similar Epithelium", the disclosure of which is provided below, or the Spirabrush™, available from The Trylon Corporation of Torrance, Calif.

Upon sampling of the lesion, the sample is stained preferably using the modified Papanicolaou stain, as is well known in the art. This stained sample is then imaged and analyzed using an image recognition system which selects abnormal cells based on a combination of abnormal morphology and abnormal keratinization particularly the characteristics associated with lesions of the oral cavity and similar epithelia.

In the preferred embodiment of the invention, the image recognition system first processes the image through an algorithmic classifier and then sends the processed data to a neural net work. The algorithmic classifier locates a first group of candidate objects within the image which could be the nuclei of cells. In accordance with the invention, the algorithmic classifier has been modified to also locate a second group of candidate objects within the image, these being cells displaying the abnormal keratinization typical of precancerous and cancerous lesions of the oral cavity. The neural net then scores cells for the presence of other morphological features associated with cancerous cells.

In one preferred embodiment of the invention, these two candidate groups are both sent to the neural net for scoring, and the highest ranking objects from the combined two groups are displayed to the expert reviewer. In an alternate embodiment of the invention, those cells displaying abnormal keratinization do not compete with other cells in the neural net stage of analysis; rather, all abnormally keratinized cells are forwarded for display to the expert reviewer.

In one preferred embodiment, the stained sample is analyzed by a modified PAPNET system, the system being modified as described herein. Such PAPNET systems are commercially available image recognition systems which select the most suspect abnormal cells and cell clusters among those presented in a stained sample, and then display these cells and cell clusters on a video monitor for expert review.

In the present state of such PAPNET systems, the programming of the system is set to detect and display the top 64 glandular cells or top 64 clusters of cells, and the top 64 squamous cells or top 64 single cells, the ratio of glandular to squamous cells or cell clusters to single cells being in a 1:1 ratio, these top cells being those cells ranked highest for abnormalities by the system.

In accordance with the present invention, the programming of the system is modified to vary this detection ratio to enhance the system's performance on oral brush biopsies of the oral mucosa. In accordance with the invention, the system is reprogrammed to detect and display the top 64 clusters of cells and the top 128 single cells, in a 1:2 ratio. Although a 1:2 ratio is used in the preferred embodiment, in other embodiments modifications can be made to the controller such that a 1:3 ratio, or some other ratio higher than 1:1 can be employed. Accordingly, by modification of this detection parameter the detection capabilities for abnormalities in oral lesions is improved.

In its current form, the commercially available PAPNET system is programmed to analyze the visual image of the stained sample to detect abnormalities consistent with the presence of a cancerous or precancerous condition. In accordance with the present invention, the current programming is still utilized and such abnormalities are located. However, in addition thereto, the system is reprogrammed such that a further set of parameters are introduced to enhance the system's detection capabilities, by isolating a second group of candidate cells. Specifically, in the preferred embodiment of the invention, the image recognition system is directed to enhance its detection of abnormalities of the oral cavity by including a function to detect abnormalities such as are characteristic of dysplastic and cancerous oral tissue. In the preferred embodiment, the system detects abnormal keratin. These keratinized cells are then either forwarded to the neural net for detection of abnormalities consistent with cancer or precancer, or are forwarded directly to an expert for analysis.

Another method to detect abnormal samples is to set threshold levels for morphology and/or color, which threshold levels indicate, if exceeded, that there is a likelihood of abnormal cells in the sample being analyzed.

Research has indicated that lesions of the oral cavity and similar epithelium often display a progressive keratinization. This process o f keratinization occurs throughout the epithelial layers. These keratins typically occur uniformly throughout the cytoplasm. In accordance with the present invention, several morphologic features present in the routine Papanicolaou stain are used to facilitate the detection and identification of these keratins. The most distinctive characteristic of the presence of the more mature keratins is a hyalinization, or glassy appearance to the cytoplasm. As Frost has described, for example, this hyaline character often imparts to the cytoplasm "the impression of viewing a brilliantly gleaming colored glass of a stained glass window, with the sun beaming in from behind." Other observers have described the appearance as "shiny", "metallic" or "glowing." A second important characteristic associated with these keratins is the presence of a particular color. As the process of keratinization develops, samples obtained by staining change from basophilia (i.e. green to blue) toward acidophilia (e.g. yellow or orange to red). In accordance with the present invention, an orange to red color is looked for, or a deep 'Halloween orange'.

Accordingly, in the preferred embodiment of the invention, the PAPNET system is redesigned or reprogrammed to detect "glowing" or glassy, orange-red cytoplasms, as are associated with abnormal keratinization of oral and similar epithelia. In the preferred embodiment, the algorithmic classifier is programmed to take the cells of the stained sample and to further perform an analysis of their color. In one embodiment, each pixel of the image is separately screened or tested for distinctive color characteristics. In an alternative embodiment, the cells are first screened and detected for abnormality by the system using the standard parameters of the PAPNET system (with a modified detection ratio as described above) and are then analyzed for distinctive color.

In this color detection step of the preferred embodiment, every pixel of the image is preferably measured to detect the pixel's Hue (H), Intensity (I) and Saturation (S). The target Hue sought is an orange-red, such as that commonly associated with abnormally keratinized cytoplasm. In one preferred embodiment, the system searches for a Hue of approximately 46–82 on a scale ranging from 0–255. In addition to Hue, the target pixels which the system searches for are those cells which further have a high Intensity and a high Saturation. Specifically, in one preferred embodiment, the system is set to search for and detect pixels with an Intensity of 100–255 on a range of 0–255. Likewise, in the preferred embodiment, the system is set to detect a Saturation of 43–255, also on a range of 0–255.

Having been set with the desired parameters of H, I and S, in the preferred embodiment the system is programmed to analyze each pixel of the sample image and to narrow down the target pixels of interest to those pixels displaying all of the preferred parameters of desired Hue, Intensity and Saturation. RGB analysis could also be employed.

Once the pixels with the desired color characteristics have been isolated, a morphological closing, i.e. a dilation and an erosion, is mathematically performed by the system to find round objects. Such closings are known in the art, and are used, for example, elsewhere in the prior unmodified PAPNET system for purposes unrelated to the detection of abnormal keratin. Likewise, Pratt describes such closings and the mathematics of the same. See, William K. Pratt, Digital Image Processing, Second Edition, Chapter 15, Morphological Image Processing (New York: John Wiley & Sons).

In accordance with the present invention, the morphological closing operation on these pixels with the desired color characteristics is performed using a 9×9 (octogonal) structuring element. (The 14×14 structuring element used by the PAPNET system in a separate step unrelated to color processing can still be used, however, in that separate step of the image processing). The 9×9 structuring element used in this stage of the process tends to find round objects, and will find those which are approximately 2–18 microns in diameter.

Once this closing has been performed, a sizing is performed. In this step, objects under 10 microns in diameter are rejected from consideration. Such filtration of objects based on size is well known in the art, having been used in other applications, among them the unmodified PAPNET system, and is discussed, for example, in U.S. Pat. No. 5,257,182 issued to Luck et al., and entitled "Morphological Classification System and Method".

Once this sizing step has been conducted, the system has now effectively selected round objects with a glowing cytoplasm that meet the criteria of abnormally keratinized cells of the oral cavity. The system then cuts out a window of approximately 48 microns by 48 microns around the centroid of each such object, forming the second group of candidate objects.

In the preferred embodiment of the invention, the first group of candidate objects (those objects which have been isolated by the algorithmic classifier without reference to color characteristics) and the second group of candidate objects (those cells isolated based on color characteristics that indicate the presence of abnormal keratinization) are both sent to the neural net for scoring, and the highest ranking objects from the combined two groups are displayed to the expert reviewer.

Figure 2:
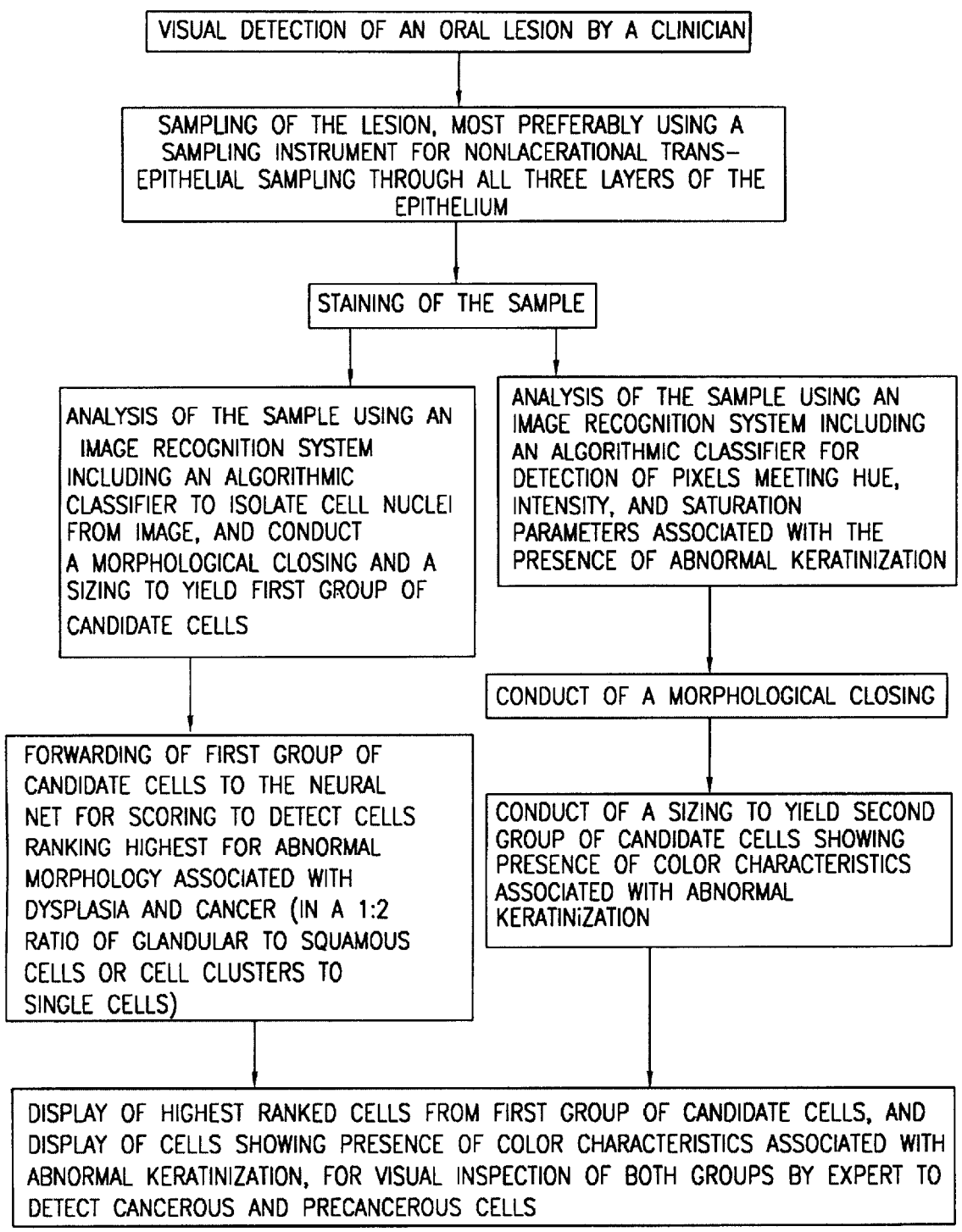
FIG. 2 is a flowchart illustrating the method of an alternate embodiment, in accordance with the present invention.

In an alternate embodiment of the invention, as shown in FIG. 2, those cells displaying abnormal keratinization do not compete with other cells in the neural net stage of analysis. Rather, the first group of candidate cells is scored by the neural net, and the second group of candidate cells bypasses the neural net and is directly forwarded for display to the expert reviewer.

Figure 3:
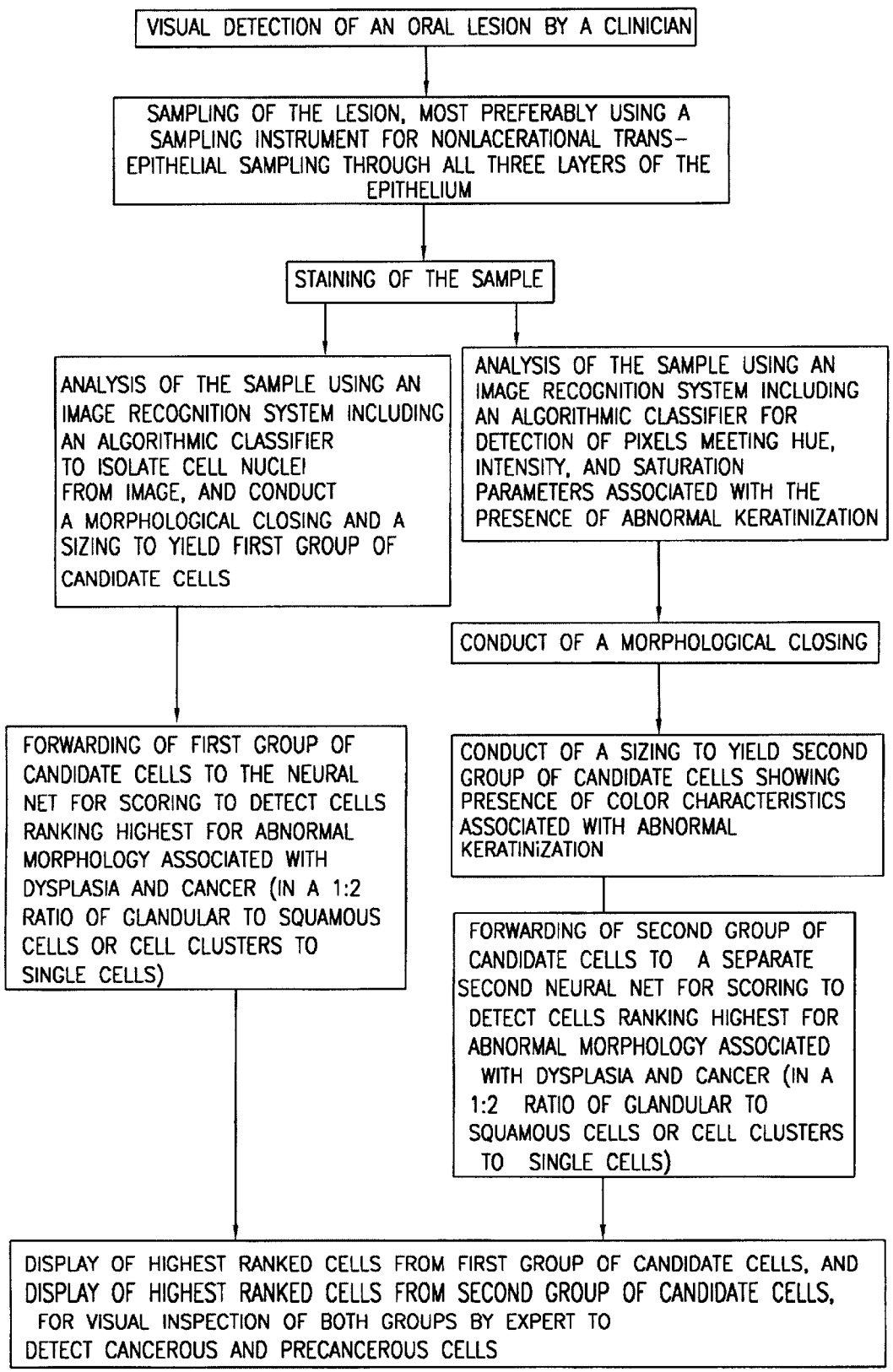
FIG. 3 is a flowchart illustrating the method of a third embodiment, in accordance with the present invention.

In yet a further alternate embodiment of the invention, as shown in FIG. 3, those cells displaying abnormal keratinization are sent to a separate, second neural net for independent ranking by a neural net, but also without having to compete with other cells in the neural net stage of analysis. Thus, the first group of candidate cells is scored by a first neural net, and the second group of candidate cells is scored by a second neural net, with each group of cells being forwarded for display to the expert reviewer.

A pathologist, cytologist or other expert reviewer can then visually examine the objects forwarded for the display, the objects being displayed on a video monitor. Upon visual inspection, the reviewer can then make a determination whether a cancerous or precancerous condition is present. Preferably, in accordance with the invention, the image recognition system also provides a color printout of those suspect cells and cell clusters selected by the expert reviewer as representative of the case.

An alternative embodiment to scoring and displaying the cells to an expert reviewer is to program the system to set certain threshold levels both for morphological abnormalities and/or abnormal keratinization. When those threshold levels are exceeded, the system will automatically produce a visualization of only such specific cells and not those highest scored or highest ranked on the specimen regardless of whether or not the scores have exceeded the threshold level.

In a further embodiment of the invention, the system can be programmed to detect and display basal cells using a basal cell detector in the algorithmic classifier. Alternatively, the pathologist can merely examine the cells in the sample with a standard microscope to detect the presence of basal cells. This embodiment provides a "fail-safe feature" within the overall testing process to ensure that a transepithelial sample has been obtained, i.e. that the cellular sample includes cells from all three layers of the epithelia. Should the pathologist determine that basal cells are not, in fact, present, the incomplete sample can be disregarded if negative and sampling can be repeated to attempt to obtain a tranepithelial sample for analysis. In this manner, the pathologist will not rely on the incomplete sample for the test results. Thus, if the initial sampling fails to obtain a transepithelial sample, that deficiency is detected in advance and the patient will not obtain a false sense of security from a false negative.

The PAPNET system, as is commercially available was designed for a platform with a neural network which has relatively slow processing speeds. Because of the large number of cells in the original sample requiring examination, and the speed of the original PAPNET neural network, a multiple stage analysis was performed in which the population of cells to be analyzed by the neural network was necessarily reduced at each stage to allow the overall process to run in a reasonable time. For example, if 500,000 cells were in a sample, a first analytical stage applying algorithmic, first stage neural network or other analytical techniques could reduce that population to approximately 50,000 cells, which could then be realistically examined by the processing speed of the then available neural networks.

Due to the increased speed of microprocessors and computers, the decisional analysis to determine either threshold level crossings, color analysis or morphological analysis can be accomplished with a single stage neural network. A single stage neural network is meant to indicate that there may be different layers within the neural network, but the entirely of the process can occur in a single stage without prior elimination of objects requiring neural network analysis.

With current processors, such as a Pentium 300, a single neural network stage can be implemented in which the entirety of the population of sample cells can be analyzed in a sufficiently short period of time to realize practical operation.

The following is the disclosure of U.S. Provisional Patent Application Ser. No. 60/093,910, filed Jul. 23, 1998 and entitled "Apparatus and Method for Performing a Non-Lacerating Biopsy of Lesions of the Oral Cavity and of Similar Epithelium." In order to avoid confusion, numbering of figures and elements has been changed from those used in the original disclosure.

Figure 6:
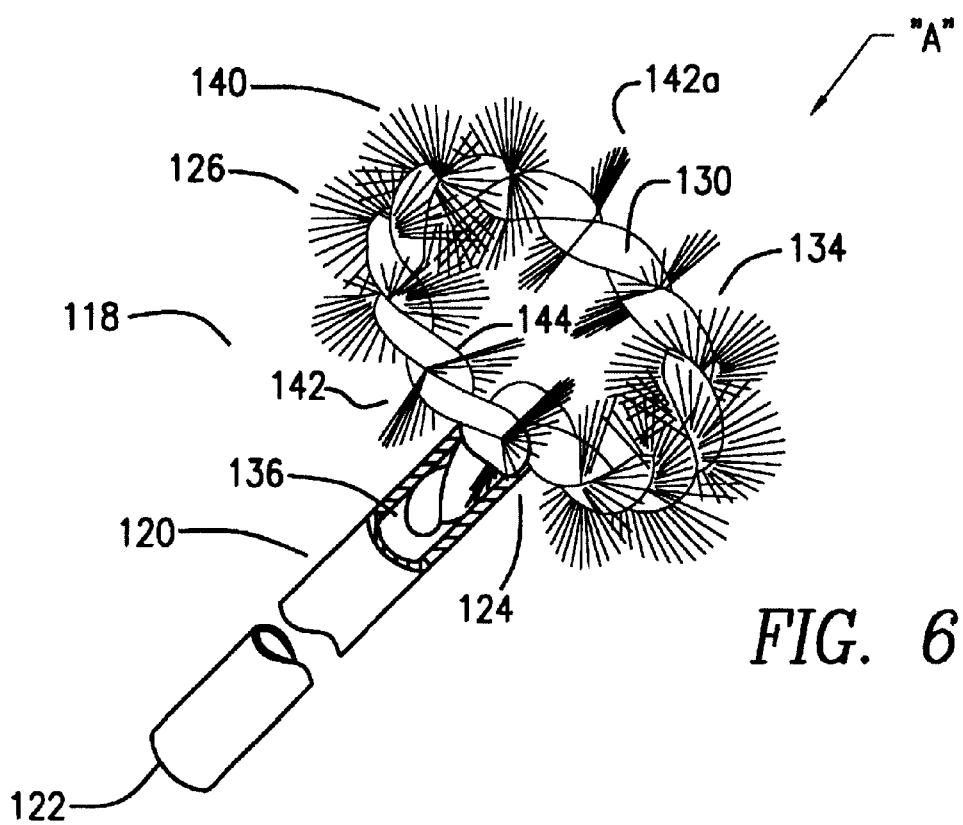
FIG. 6 is a perspective view of an apparatus for sampling epithelial tissue in accordance with the present invention.

A preferred embodiment of the invention is provided in FIG. 6. In accordance with the invention, a device is provided which comprises a handle or elongate member 120, having both a proximal end 122 and a distal end 124. In the preferred embodiment, the total length of the device is approximately six inches.

Handle 120 is designed for gripping by a user, and is of a sufficient length to allow the user to manipulate the device within a body cavity from a location just outside the body. In the preferred embodiment, handle 120 is semi-rigid so as to assist in reaching the target tissue notwithstanding difficult angles or narrow passages. In the preferred embodiment, the handle is approximately 5 inches long.

The brush handle can be constructed of a plastic, such as polypropylene, or any other suitable semi-rigid material. The handle can be solid, but is hollow in the preferred embodiment. It is further preferred that handle 120 also have at least one area whose crosssection is substantially circular such that the elongate member may be readily twirled between the thumb and forefinger.

At or around the distal end 124 of the handle or elongate member 120, the device is provided with a brush head 126. Brush head 126 is preferably a substantially toroidal or "donut" shaped brush, and can be formed from one or more twisted or braided wires or cables 130. Wires or cables 130 are preferably secured to handle 120 by affixation of both ends of the wire 130 in a recess 136 located in the proximal end 124 of the handle. Wires 130 are preferably constructed of twisted metal. In a preferred embodiment, the total length of the twisted wire is approximately 1.1 inches, with approximately 0.2 inches inserted in the handle, and approximately 0.9 inches exposed as part of the toroid. In the method of the invention, this metal is used to apply pressure to the epithelia, while the bristles are used to collect the desired cells.

Wires or cables 130 are preferably bent to form a toroid 134 which is perpendicular to the longitudinal axis of handle 120. In other words, toroid 134 preferably defines a circular plane, the plane being provided perpendicular to the longitudinal axis of the handle 120 of brush head 126. Alternatively, a cross-section of the brush forms a nautilus or spiral shape at ninety degrees to the handle or elongate member 120.

Brush head 126 may be integral with handle 120, or may be detachable. Alternatively, the proximal end 122 of the handle 120 may be detachable from the distal end 124. The detachable portion of the brush may be scored, to easily break away, may be provided with screw threads to screw off the remainder of the device, or so forth. In either embodiment, detachment of either the brush head or of a portion of the handle connected to the brush head, can allow the distal end of the brush, having sampled cells collected therein, to be separated from the proximal end. This allows the handle or the proximal end thereof to be discarded while the distal end of the apparatus is forwarded to the laboratory for analysis. For example, the distal portion of the device can be dropped into solution, while the proximal portion is thrown away.

Brush head 126 is further provided with a plurality of bristles 140. In the preferred embodiment, bristles 140 are approximately 0.11 mm in width, and 0.25 inches in length.

Although in the prior art, the sampling brushes provided have been soft brushes with soft bristles, in the present invention, bristles 140 are specifically made stiff or semi-rigid, going against the teachings of the art. As described above, for example, U.S. Pat. No. 4,759,376 teaches that the bristles of the brush should be relatively soft and should readily bend Likewise, the brush disclosed in U.S. Pat. No. 4,762,133, is also meant to be soft, as is it provided for sampling the exocervix along with the endocervix. This preference heretofore in the art to use a soft brush prevents causing damage to tissue. While this is generally desirable in the cervix, it is not helpful when the lesions are keratinized, as in the oral cavity.

Moreover, sampling below the superficial layer of the epithelium is not sufficiently or consistently achieved with prior art brushes. In contrast, in the present invention, it is specifically desired to damage the tissue of a lesion and penetrate beneath the superficial layer of the epithelium to sample all three epithelial layers. Whereas the prior art brushes are generally designed for the cervix where no keratin is present, the present brush can penetrate through keratin covered lesions to provide a suitable tissue sample.

Accordingly, in the present invention, bristles 140 of brush head 126 are each stiff or semi-rigid. The bristles are preferably made of double density Tynex® brand nylon, and have a diameter of between 0.001 cm and 0.015 cm, or between 0.004 cm and 0.01 cm, or between 0.005 and 0.007 cm. Preferably, the bristles have a diameter of approximately 0.006 cm. Although triple and single density bristles may be used, double density bristles are preferred for their ability to balance surface area for abrasion with inter-bristle space for the collection of cells. The bristles further have a tangent modulus or stiffness greater than 890,000 psi, and preferably greater than 1,000,000 psi. The upper limit on stiffness should approximately be that of steel to avoid bleeding or trauma to the tissue.

Bristles 140 are preferably provided in a series of fan-like arrays 142. As shown in FIG. 6, each fan-like array 142 is composed of a series of bristles 140, the bristles extending radially from a center 144, to form each of the fan-like arrays 142. At center 144, the end of each bristle 140 is secured within the twisted wire 30 backbone.

Figure 7:
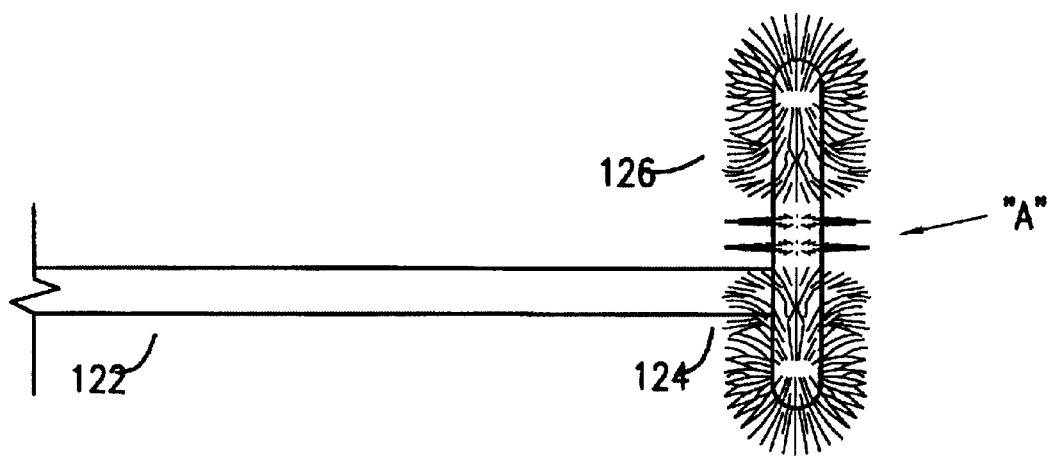
FIG. 7 is a side view of the apparatus for sampling epithelial tissue shown in FIG. 1.

Fan-like arrays 142 preferably extend around the entire perimeter of toroid 134. In the preferred embodiment, viewing the apparatus head-on, from the perspective "A" in FIGS. 6 or 7, twelve fan-like arrays or tufts of bristles are evenly arranged around the perimeter of the toroid. Thus, the arrays are arranged at 130 degrees spacings along the twisted wire of the brush head.

In the preferred embodiment, each fan-like array 142 is "cupped". In other words, the bristles do not form a plane, but rather preferably extend upward from center 144 at an acute angle to wire 130. As a result of this bristle orientation, clockwise rotation (or counterclockwise rotation depending on the direction of the acute bristle angle with respect to the handle) will result in a degree of bristle abrasion that is moderated due to the avoidance of direct piercing of the skin with the stiff bristle ends. Rotation in the opposite direction will result in abrasion that is greatly accentuated by maximizing the direct piercing of the skin with the stiff bristle ends. While the unique drilling combination of bristle pressure, stiffness, and rotation results in provision of the trans-epidermal cytological sample of the lesion as noted above, rotation in the direction which moderates direct surface piercing by the bristle ends (clockwise, in the case of the preferred embodiment) allows this trans-epidermal cytologic sample to be obtained with minimal discomfort to the patient.

The brush's stiff bristles form a substantially flat application plane that can grip the often wet and slippery surface of an oral cavity lesion with sufficient traction to avoid inadvertent slippage. Substantial flatness at the point of application also results in continuous abrasion of tissue during rotation of the device.

The present invention allows for limited space between the points of abrasive contact upon brush rotation, while maintaining enough separation between the bristles to trap a clinically effective amount of cells. The length of the stiff bristles of the brush may also vary but is similarly balanced between: 1) the requirement to keep the bristles stiff enough to grind the tissue into its cellular components during rotation; and 2) the requirement that the bristles be long enough to trap the removed cells. In a preferred embodiment, the bristles are approximately 0.25 inches in length.

Figure 8:
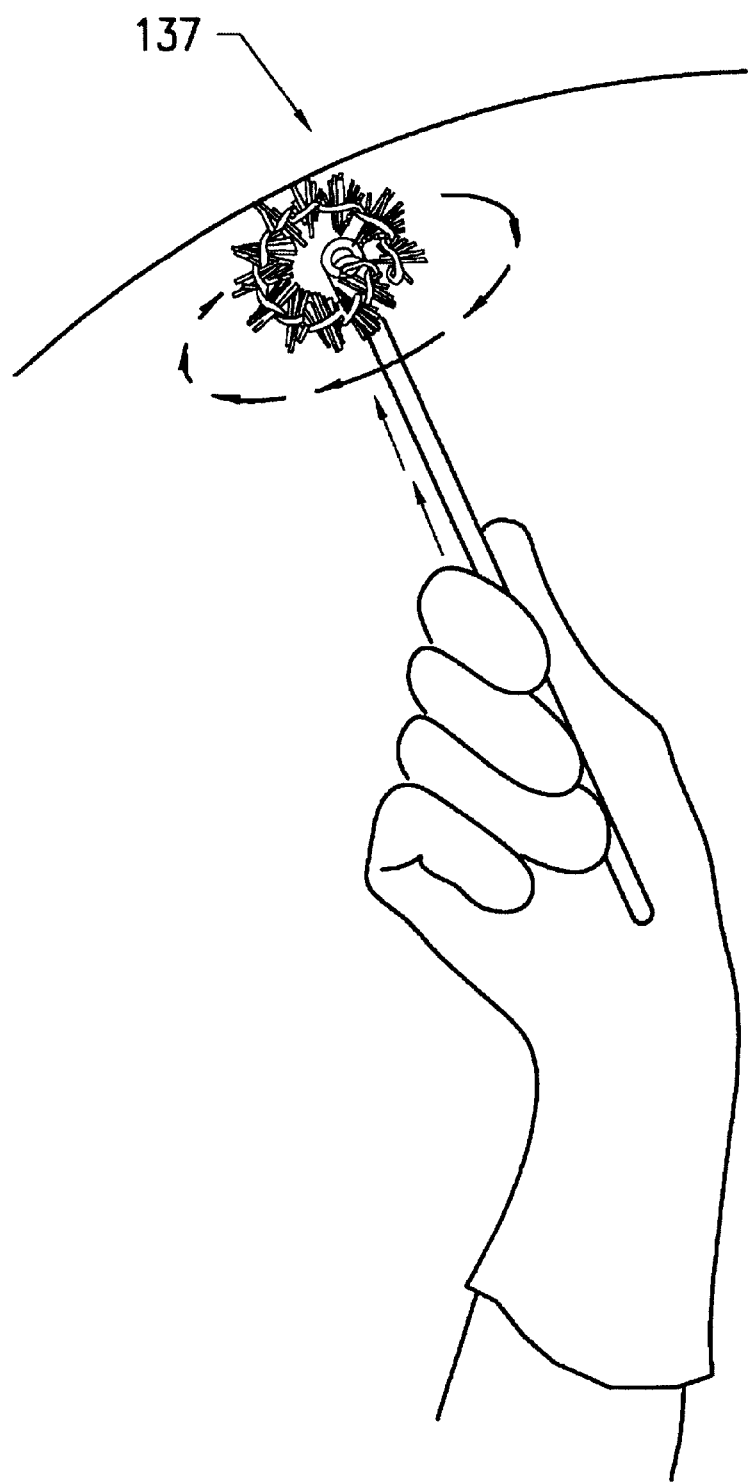
FIG. 8 illustrates the use of the apparatus of FIG. 6.

As shown in FIG. 8, according to the method of the present invention, the flat distal end of the handle of the brush is placed directly on the site of the visibly observed suspect lesion 137. The stiff dense bristles are then pushed firmly against the lesion site while the handles is simultaneously rotated clockwise at least once, and preferably several times about its axis. The metal or twisted wire of the brush head assists in the application of pressure to the epithelial surface.

Rotation of the bristles against the lesion results in the frictional detachment of cells from multiple layers of the epithelium. The detached cells become collected between the stiff bristles and trapped within the space defined by the opening in the toroid. These cells can then be tested by a suitable laboratory.

The method of the present invention is particularly advantageous due to the fact that, as no laceration of the epithelium is required, the discomfort experienced by the patient is considerably less than that of a surgical biopsy, and is generally minimal.

The method of the present invention is in contrast to the method of the prior art, in which the technique has been to "sweep" the soft bristles of a brush or other non-abrasive instrument over and across the surface of a lesion. In the present invention, the stiff bristles are pressed down and rotated into a lesion of potential concern to penetrate or "drill" into the lesion. This drilling presents the ability to thoroughly sample all layers of the epithelia without the necessity of performing a surgical laceration. Specifically, the preferred embodiment's unique combination of: 1) strong manual pressure transferred directly by the handle of the device to the interface between the flat surface of the brush and the surface of the lesion; 2) the high degree of bristle stiffness, and, 3) rotation of the device, provide this superior "drilling" action into the epithelium which has previously been unknown in the art of cytology. It is this unique drilling action which results in the unique and improved ability of the subject invention to provide a cytological sample of a keratinized lesion which contains cells from all epidermal layers of the underlying epithelium.

As such, the cytologic sample obtained by the present invention is the functional equivalent of the tissue core type of sample taken by the prior art lacerating biopsy technique, and yet is obtained without the patient discomfort, scarring, and other difficulties potentially associated with a lacerating biopsy.

Moreover, in addition to avoiding patient discomfort and scarring, the present invention poses yet a further advantage over the prior art lacerating technique. In the present invention, a sample can be obtained from the entire surface of a multifocal lesion to provide a broad sample of cells from the entire lesion for further testing. In contrast, in the prior art incisional surgical biopsy a tissue core is taken of only a portion of a lesion to test the lesion for malignancy. Accordingly, due to the fact that the particular portion of the lesion sampled by the surgical technique may be benign, while a non-sampled portion of the lesion may be malignant, false negatives may potentially occur. The present invention's broad sampling of a lesion avoids this potential problem. Thus, it is further preferred, in accordance with the method, that the brush be rotated over the entire surface of a lesion, and not just a portion thereof, to ensure that sampling is as thorough as possible in the event that the lesion is multifocal. In this manner, the invention avoids the disadvantages of the prior art.

In a clinical study, a group of patients with visible oral lesions were tested using cytological samples obtained with the preferred embodiment of the subject invention. In all cases the subject invention resulted in a trans-epidermal sample of the suspect lesion. That is, in every sample taken cells were obtained from the basal, intermediate, and superficial layers of the oral epidermis. In a subset of these cases, a matching lacerating biopsy was also performed of the same lesion. In all cases in that subset, correlation between the cytological smear obtained with the subject invention and the histological diagnosis obtained with a lacerating biopsy was perfect for the detection of pre-cancer and cancer. These results were achieved using the subject invention without a single report of patient discomfort, the requirement of any form of local anesthetic, or scarring as would be expected with the lacerating biopsy technique.

Use of the subject invention is not limited to the oral cavity, but extends to other epithelia where a lesion requiring diagnosis may be observed, where exfoliation of cells is limited by the presence of keratin or other factors, and where an alternative to a lacerating biopsy is desired. Cytological testing of observed lesions of the vulva is one such example of an alternate potential use of the subject invention.

Having described this invention with regard to specific embodiments, it is to be understood that the description is not meant as a limitation since further embodiments, modifications and variations may be apparent or may suggest themselves to those skilled in the art. It is intended that the present application cover all such embodiments, modifications and variations.

What is claimed is:

1. Apparatus to detect abnormal cells in epithelial tissue of the body comprising:

transepithelial non-lacerational sampling means to collect calls from at least two layers of said epithelial tissue, analytical apparatus to analyze said cells collected by said transepithelial sampling means to detect abnormal cells, wherein said transepithelial non-lacerational sampling means collects cells from three layers of said epithelial tissue, said three layers comprising superficial, intermediate and basal layers, wherein said analytical apparatus comprises means to detect whether or not cells from said basal layer are detected.

2. Apparatus to detect abnormal cells in epithelial tissue of the body according to claim 1, wherein said epithelial tissue comprises keratinized cells.

3. Apparatus to detect abnormal cells in epithelial tissue of the body according to claim 2, wherein said transepithelial sampling means comprises an abrasive sampling structure.

4. Apparatus to detect abnormal cells in epithelial tissue of the body according to claim 2, wherein said sampling means comprises a brush.

5. Apparatus to detect abnormal cells in epithelial tissue of the body according to claim 2, wherein said keratinized cells include abnormally keratinized cells.

6. Apparatus to detect abnormal cells in epithelial tissue of the body according to claim 2, wherein said epithelial tissue comprises oral epithelial tissue.

7. Apparatus to detect cells with abnormal morphology in epithelial tissue of the body according to claim 2, wherein said epithelial tissue is located in the areas of the body selected among the group comprising the larynx, pharynx, esophagus and vulva.

8. Apparatus to detect abnormal cells in epithelial tissue of the body according to claim 2, wherein said abnormal cells have a high probability of exhibiting cancerous conditions.

9. Apparatus to detect abnormal cells in epithelial tissue of the body according to claim 2, wherein said abnormal cells have a high probability of exhibiting non-cancerous conditions.

10. Apparatus to detect abnormal cells in epithelial tissue of the body according to claim 9, wherein said non-cancerous conditions are selected from the group comprising candidiasis, herpes, geographic tongue, lichenplanus, and human papilloma virus.

11. Apparatus to detect abnormal cells in epithelial tissue of the body according to claim 2, wherein said analytical apparatus further comprises an image recognition system imaging said abnormal cells.

12. Apparatus to detect abnormal cells in epithelial tissue of the body according to claim 11, wherein said image recognition system comprises means to select the most suspect abnormal cells among the cells sampled and means to image said suspect cells.

13. Apparatus to detect abnormal cells in epithelial tissue of the body according to claim 12, wherein said image recognition system further comprises means to produce a color image of said suspect cells.

14. Apparatus to detect abnormal cells in epithelial tissue of the body according to claim 11, wherein said image recognition system displays said abnormal cells to be viewed.

15. Apparatus to detect abnormal cells in epithelial tissue of the body according to claim 11, wherein said analytical image recognition system comprises an algorithmic classifier.

16. Apparatus to detect abnormal cells in epithelial tissue of the body according to claim 11, wherein said image recognition system comprises means to detect color properties of the sample.

17. Apparatus to detect abnormal cells in epithelial tissue of the body according to claim 16, wherein said image recognition system comprises means to detect color properties associated with abnormal keratinization.

18. Apparatus to detect abnormal cells in epithelial tissue of the body according to claim 17, further comprising means to conduct a morphological closing, further comprising means to conduct a sizing to produce a first group of candidate cells.

19. Apparatus to detect abnormal cells in epithelial tissue of the body according to claim 18, wherein said apparatus further comprises means to produce a second group of candidate cells related to the detected color properties.

20. Apparatus to detect abnormal cells in epithelial tissue of the body according to claim 19, further comprising means to analyze said first and second groups of candidate cells to rank those cells having the highest probability for being abnormal cells.

21. Apparatus to detect abnormal cells in epithelial tissue of the body according to claim 18, wherein said apparatus further comprises means to reject objects under $10\mu$ in diameter.

22. Apparatus to detect abnormal cells in epithelial tissue of the body according to claim 16, further comprising means to display a selected group of said cells having said highest probability.

23. Apparatus to detect abnormal cells in epithelial tissue of the body according to claim 22, wherein said apparatus comprises means to detect cell size of approximately $2-18\mu$ in diameter.

24. Apparatus to detect abnormal cells in epithelial tissue of the body according to claim 11, wherein said image recognition system and said analytical apparatus comprises means to set a threshold level relating to the characteristics of the cells sampled by said sampling means, and means to detect when the characteristics of said cells of said sampling means exceed said threshold level.

25. Apparatus to detect abnormal cells in epithelial tissue of the body according to claim 24, wherein the characteristics of the cells sampled for which a threshold level is set relate to the color characteristics thereof.

26. Apparatus to detect abnormal cells in epithelial tissue of the body according to claim 25, wherein the color characteristics relate to the appearance of abnormal keratinization.

27. Apparatus to detect abnormal cells in epithelial tissue of the body according to claim 25, wherein the characteristics of the sample cells relate to morphological characteristics.

28. Apparatus to detect abnormal cells in epithelial tissue of the body according to claim 24, wherein the characteristics relate to the appearance of abnormal keratinization.

29. Apparatus to detect abnormal cells in epithelial tissue of the body according to claim 28, wherein the characteristics of the sample cells relate to morphological characteristics.

30. Apparatus to detect abnormal cells in epithelial tissue of the body according to claim 2, wherein said cells are stained to produce a stained appearance of abnormal keratin.

31. Apparatus to detect abnormal cells in epithelial tissue of the body according to claim 2, further comprising an automated image processing system for detection of abnormal keratinization.

32. Apparatus to detect abnormal cells in epithelial tissue of the body according to claim 2, further comprising means to stain said cells which are collected from said transepithelial sampling means wherein said apparatus analyzes said stained cells.

33. Apparatus to detect abnormal cells in epithelial tissue of the body according to claim 1, wherein said transepithelial sampling means comprises an abrasive sampling structure.

34. Apparatus to detect abnormal cells in epithelial tissue of the body according to claim 1, wherein said sampling structure comprises a brush.

35. Apparatus to detect abnormal cells in epithelial tissue of the body according to claim 34, wherein said brush comprises a nylon brush having bristles which are rotated over the epithelial tissue from which samples are to be taken for analysis.

36. Apparatus to detect abnormal cells in epithelial tissue of the body according to claim 35, wherein said brush comprises a circular stiff nylon brush.

37. Apparatus to detect abnormal cells in epithelial tissue of the body according to claim 1, wherein said epithelial tissue comprises oral epithelial tissue.

38. Apparatus to detect cells with abnormal morphology in epithelial tissue of the body according to claim 1, wherein said epithelial tissue is located in the areas of the body selected among the group comprising the larynx, pharynx, esophagus and vulva.

39. Apparatus to detect abnormal cells in epithelial tissue of the body according to claim 1, wherein said abnormal cells have a high probability of exhibiting cancerous conditions.

40. Apparatus to detect abnormal cells in epithelial tissue of the body according to claim 1, wherein said abnormal cells have a high probability of exhibiting non-cancerous conditions.

41. Apparatus to detect abnormal cells in epithelial tissue of the body according to claim 40, wherein said non-cancerous conditions are selected from the group comprising candidiasis, herpes, geographic tongue, lichenplanus, and human papilloma virus.

42. Apparatus to detect abnormal cells in epithelial tissue of the body according to claim 1, wherein said analytical apparatus further comprises an image recognition system imaging said abnormal cells.

43. Apparatus to detect abnormal cells in epithelial tissue of the body according to claim 42, wherein said image recognition system comprises means to select the most suspect abnormal cells among the cells sampled and means to image said suspect cells.

44. Apparatus to detect abnormal cells in epithelial tissue of the body according to claim 43, wherein said image recognition system further comprises means to produce a color image of said suspect cells.

45. Apparatus to detect abnormal cells in epithelial tissue of the body according to claim 42, wherein said image recognition system displays said abnormal cells to be viewed.

46. Apparatus to detect abnormal cells in epithelial tissue of the body according to claim 42, wherein said image recognition system detects cells collected by said sampling means which exhibit abnormal morphology, said image recognition system further comprises an algorithmic classifier.

47. Apparatus to detect abnormal cells in epithelial tissue of the body according to claim 46, wherein said apparatus further comprises means to conduct a morphological closing.

48. Apparatus to detect abnormal cells in epithelial tissue of the body according to claim 47, wherein said image recognition system comprises means to conduct a sizing to yield a first group of candidate cells.

49. Apparatus to detect abnormal cells in epithelial tissue of the body according to claim 42, wherein said apparatus detects cells collected by said sampling means which exhibit abnormal morphology.

50. Apparatus to detect abnormal cells in epithelial tissue of the body according to claim 49, wherein said apparatus comprises means to detect cell size of approximately 2–18$\mu$ in diameter.

51. Apparatus to detect abnormal cells in epithelial tissue of the body according to claim 50, wherein said apparatus further comprises means to reject objects under 10$\mu$ in diameter.

52. Apparatus to detect abnormal cells in epithelial tissue of the body according to claim 42, further comprising means to stain said cells which are collected from said transepithelial sampling means wherein said apparatus analyzes said stained cells.

53. Apparatus to detect abnormal cells in epithelial tissue of the body according to claim 52, wherein said apparatus which analyzes said stained cells includes an algorithmic classifier to isolate cell nuclei from the image produced by said image recognition system, further comprising means to conduct a morphological closing and to conduct a sizing to yield a first group of candidate cells.

54. Apparatus to detect abnormal cells in epithelial tissue of the body according to claim 53, wherein said image recognition system includes an algorithmic classifier for detecting parameters associated with the presence of keratin, conducting a further morphological closing of said sample analyzing the presence of keratin, and conducting a sizing to yield a second group of candidate cells from said cells which contain keratin and have had a morphological closing.

55. Apparatus to detect abnormal cells in epithelial tissue of the body according to claim 54, further comprising a neural network to analyze said first group of candidate cells and said second group of candidate cells to rank those having the highest abnormal morphology, and means to display a subset of said cells.

56. Apparatus to detect abnormal cells in epithelial tissue of the body according to claim 54, wherein said image recognition system comprises means to display the highest ranked cells from the first group of candidate cells and display of cells showing presence of color characteristics associated with abnormal keratinization for visual inspection.

57. Apparatus to detect abnormal cells in epithelial tissue of the body according to claim 42, wherein said image recognition system and said analytical apparatus comprises means to set a threshold level relating to the characteristics of the cells sampled by said sampling means, and means to detect when the characteristics of said cells of said sampling means exceed said threshold level.

58. Apparatus to detect abnormal cells in epithelial tissue of the body according to claim 57, wherein the characteristics of the sample cells relate to morphological characteristics.

59. Apparatus to detect abnormal cells in epithelial tissue of the body according to claim 1, wherein said apparatus further comprises means to terminate said analysis when said apparatus determines that cells from said basal layer have not been selected.

60. Apparatus to detect abnormal cells in epithelial tissue of the body according to claim 1, further comprising means to stain said cells which are collected from said transepithelial sampling means wherein said apparatus analyzes said stained cells.

* * * * *